United States Patent
Fox (10) Patent No.: US 9,579,482 B2
(45) Date of Patent: Feb. 28, 2017

(54) SYSTEM AND METHOD FOR A WAKEFUL SLEEP DETECTION ALARM

(71) Applicant: KONINKLIJKE PHILIPS N.V., Eindhoven (NL)

(72) Inventor: Nathaniel Solomon Fox, Pittsburgh, PA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/383,243

(22) PCT Filed: Mar. 28, 2013

(86) PCT No.: PCT/IB2013/052480
§ 371 (c)(1),
(2) Date: Sep. 5, 2014

(87) PCT Pub. No.: WO2013/144893
PCT Pub. Date: Oct. 3, 2013

(65) Prior Publication Data
US 2015/0080642 A1    Mar. 19, 2015

Related U.S. Application Data

(60) Provisional application No. 61/616,478, filed on Mar. 28, 2012.

(51) Int. Cl.
*G08B 23/00* (2006.01)
*A61M 21/00* (2006.01)
(Continued)

(52) U.S. Cl.
CPC ............... *A61M 21/00* (2013.01); *A61B 5/08* (2013.01); *A61B 5/087* (2013.01); *A61B 5/4812* (2013.01);
(Continued)

(58) Field of Classification Search
CPC .............. A61M 16/00; A61M 16/0051; A61M 16/0069; A61M 2016/0027; A61M 2016/0036; A61M 21/00; A61M 16/0003; A61M 16/0666; A61M 16/0461; A61B 5/087; A61B 5/0871; A61B 5/4806; A61B 5/4809; A61B 5/4815; A61B 5/4818; A61B 5/746; A61B 5/4812; A61B 5/08
(Continued)

(56) References Cited

U.S. PATENT DOCUMENTS

| 6,105,575 A | 8/2000 | Estes et al. |
| 2007/0023044 A1 | 2/2007 | Kwok et al. |

(Continued)

FOREIGN PATENT DOCUMENTS

| WO | 2009042454 A1 | 4/2009 |
| WO | 2011057362 A1 | 5/2011 |

*Primary Examiner* — Thomas Mullen (57) ABSTRACT

The present disclosure pertains to waking a subject from a period of wakeful sleep by modulation of a flow of breathable gas being delivered to the airway of the subject, with the modulation being performed based on a monitoring of wakefulness of the subject during sleep Typical sleep cycles comprise periods of deeper sleep and/or periods or lighter (wakeful) sleep. Waking during lighter stages of sleep may result in feeling more energetic and well-rested compared to waking from deeper sleep. Sleep therapy such as, for example, continuous positive airway pressure (CPAP), typically monitors sleep characteristics of a subject. These sleep characteristics comprise one or more of tidal volume, pressurized gas leakage (indicating movement), respiration rate, and/or other characteristics. During use of sleep therapy devices, sleep characteristics may be collected during therapy that can be used to determine whether the patient is in light sleep or deep sleep. The present disclosure contemplates utilizing a sleep therapy device in combination with (Continued)

the system described herein to collect sleep characteristics of a subject during sleep, and to wake the subject from wakeful sleep during an alarm window so the subject may feel as well rested and energetic as possible.

18 Claims, 3 Drawing Sheets

(51) Int. Cl.
    *A61B 5/00*     (2006.01)
    *A61B 5/087*     (2006.01)
    *A61M 16/00*     (2006.01)
    *A61B 5/08*     (2006.01)
    *A61M 16/04*     (2006.01)
    *A61M 16/06*     (2006.01)

(52) U.S. Cl.
    CPC .......... *A61B 5/746* (2013.01); *A61M 16/0003* (2014.02); *A61M 16/0051* (2013.01); *A61M 16/0069* (2014.02); *A61M 16/0461* (2013.01); *A61M 16/0666* (2013.01); *A61M 2016/0027* (2013.01); *A61M 2021/0083* (2013.01); *A61M 2021/0088* (2013.01); *A61M 2205/18* (2013.01); *A61M 2205/3327* (2013.01); *A61M 2205/3331* (2013.01); *A61M 2205/505* (2013.01)

(58) Field of Classification Search
    USPC ........ 340/575, 309.16; 600/300; 128/204.18, 128/204.21–204.23
    See application file for complete search history.

(56) References Cited

U.S. PATENT DOCUMENTS

2009/0082639 A1*   3/2009   Pittman ................ A61B 5/0205
                                                                            600/300
2012/0291785 A1*  11/2012  Ramanan .......... A61M 16/0051
                                                                            128/204.23

* cited by examiner

FIG. 3

SYSTEM AND METHOD FOR A WAKEFUL SLEEP DETECTION ALARM

CROSS-REFERENCE TO PRIOR APPLICATIONS

This application is the U.S. National Phase application under 35 U.S.C. §371 of International Application No. PCT/IB2013/052480, filed on Mar. 28, 2013, which claims the benefit of U.S. Provisional Patent Application No. 61/616,478, filed on Mar. 28, 2012. These applications are hereby incorporated by reference herein.

The present disclosure pertains to waking a subject from a period of wakeful sleep by modulation of a flow of breathable gas being delivered to the airway of the subject, with the modulation being performed based on a monitoring of wakefulness of the subject during sleep.

Systems for providing positive airway pressure therapy to subjects are known. These systems generate a pressurized flow of breathable gas that is provided to the airway of a subject during sleep to support the subject's airway. The support provided by the pressurized flow of breathable gas to the airway of the subject enables the subject to avoid sleep disordered breathing. A subject using positive airway pressure therapy wakes from sleep without intervention from the positive airway pressure device.

Systems for monitoring sleep are known. These systems monitor whether sleep is lighter or heavier, and can wake a subject from periods of lighter sleep. These sleep monitoring systems are not coupled to therapeutic devices and cannot alter or change sleep therapy provided to a subject during sleep.

Accordingly, one or more aspects of the present disclosure relate to a wakeful sleep detection alarm device. In some embodiments, the device comprises a pressure generator, one or more sensors, and one or more processors, wherein the one or more processors comprise a wakefulness module, an alarm module, and a control module. The pressure generator is configured to generate a pressurized flow of breathable gas for delivery to the airway of a subject. The one or more sensors are configured to generate one or more output signals conveying information related to one or more parameters of the pressurized flow of breathable gas. The one or more processors are configured to execute computer program modules. The wakefulness module is configured to determine wakefulness of the subject based on the one or more sensor output signals. The alarm module is configured to determine an alarm window of time. The control module is configured such that, responsive to the determined wakefulness of the subject breaching a threshold during the alarm window of time, the control module generates a waking stimulus. The waking stimulus comprises modulation of the pressurized flow of breathable gas.

Yet another aspect of the present disclosure relates to a method of waking a subject from sleep during a period of wakeful sleep. In some embodiments, the method comprises generating a pressurized flow of breathable gas for delivery to an airway of a subject; generating one or more output signals conveying information related to one or more parameters of the pressurized flow of breathable gas; determining wakefulness of the subject based on the one or more output signals; determining an alarm window of time; and responsive to the wakefulness of the subject breaching a threshold level during the alarm window of time, generating a waking stimulus, wherein the stimulus comprises modulation of the pressurized flow of breathable gas.

Still another aspect of the present disclosure relates to a system configured to wake a subject from sleep during a period of wakeful sleep. In some embodiments, the system comprises means for generating pressurized flow of breathable gas for delivery to an airway of a subject; means for generating one or more output signals conveying information related to one or more parameters of the pressurized flow of breathable gas; means for determining wakefulness of the subject based on the one or more output signals; means for determining an alarm window of time; and, responsive to the determined wakefulness of the subject breaching a threshold level during the alarm window of time, means for generating a waking stimulus, wherein the stimulus comprises modulation of the pressurized flow of breathable gas.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
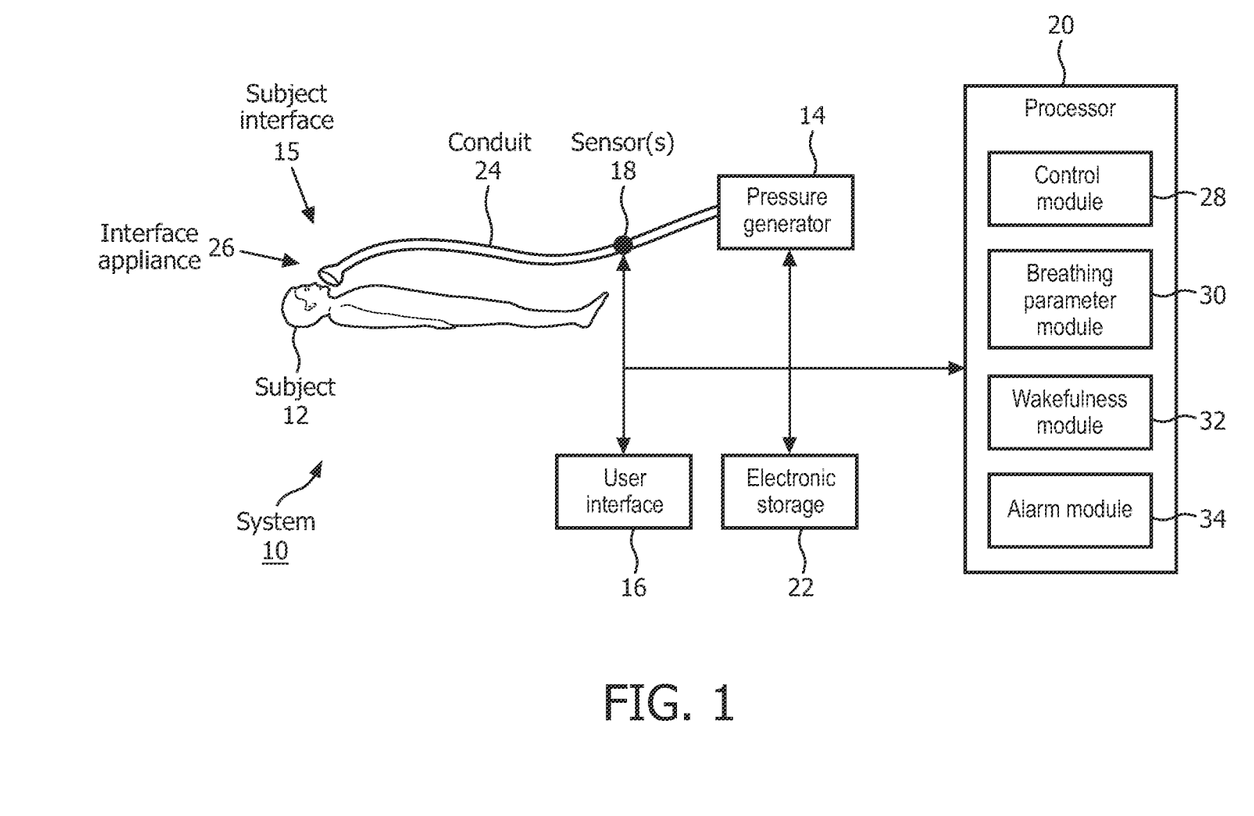
FIG. 1 is a system configured to wake a subject from wakeful sleep during an alarm window of time.

FIG. 1 schematically illustrates an exemplary embodiment of a system 10 configured to wake a subject 12 from wakeful sleep during an alarm window. Typical sleep cycles comprise periods of deeper sleep and/or periods or lighter (wakeful) sleep. Waking during lighter stages of sleep may result in feeling more energetic and well-rested compared to waking from deeper sleep. Sleep therapy such as, for example, continuous positive airway pressure (CPAP), typically monitors sleep characteristics of a subject. These sleep characteristics comprise one or more of tidal volume, pressurized gas leakage (indicating movement), respiration rate, and/or other characteristics. During use of sleep therapy devices, sleep characteristics may be collected during therapy that can be used to determine whether the patient is in light sleep or deep sleep. The present disclosure contemplates utilizing a sleep therapy device in combination with system 10 to collect sleep characteristics of subject 12 during sleep, and to wake subject 12 from wakeful sleep during an alarm window. In one embodiment, system 10 comprises one or more of a pressure generator 14, a subject interface 15, a user interface 16, one or more sensors 18, a processor 20, electronic storage 22, and/or other components.

In one embodiment, pressure generator 14 is configured to generate a pressurized flow of breathable gas for delivery to the airway of subject 12. Pressure generator 14 may control one or more parameters of the pressurized flow of breathable gas (e.g., flow rate, pressure, volume, humidity, temperature, composition, etc.) for therapeutic purposes, or for other purposes. By way of a non-limiting example, pressure generator 14 may be configured to control the pressure of the pressurized flow of breathable gas to provide pressure support to the airway of subject 12. Pressure generator 14 may include a positive pressure support device such as, for example, the device described in U.S. Pat. No. 6,105,575, hereby incorporated by reference in its entirety.

Pressure generator 14 may be configured to generate the pressurized flow of breathable gas according to one or more modes. A non-limiting example of one such mode is Continuous Positive Airway Pressure (CPAP). CPAP has been used for many years and has proven to be helpful in promoting regular breathing. Another mode for generating the pressurized flow of breathable gas is Inspiratory Positive Air Pressure (IPAP). One example of the IPAP mode is bi-level positive air pressure mode (BIPAP®). In bi-level positive air pressure mode, two levels of positive air pressure (HI and LO) are supplied to a patient. Other modes of generating the pressurized flow of breathable gas are contemplated. Generally, the timing of the HI and LO levels of pressure are controlled such that the HI level of positive air pressure is delivered to subject 12 during inhalation and the LO level of pressure is delivered to subject 12 during exhalation.

The pressurized flow of breathable gas is delivered to the airway of subject 12 via a subject interface 15. Subject interface 15 is configured to communicate the pressurized flow of breathable gas generated by pressure support generator 14 to the airway of subject 12. As such, subject interface 15 comprises a conduit 24 and an interface appliance 26. Conduit 24 conveys the pressurized flow of breathable gas to interface appliance 26, and interface appliance 26 delivers the pressurized flow of breathable gas to the airway of subject 12. Some examples of interface appliance 26 may include, for example, an endotracheal tube, a nasal cannula, a tracheotomy tube, a nasal mask, a nasal/oral mask, a full face mask, a total face mask, or other interface appliances that communicate a flow of gas with an airway of a subject. The present disclosure is not limited to these examples, and contemplates delivery of the pressurized flow of breathable gas to subject 12 using any subject interface.

User interface 16 is configured to provide an interface between system 10 and subject 12 through which subject 12 may provide information to and receive information from system 10. This enables data, results, and/or instructions and any other communicable items, collectively referred to as "information," to be communicated between the subject 12 and one or more of pressure generator 14, and/or processor 20. Examples of interface devices suitable for inclusion in user interface 16 include an alarm clock, a keypad, buttons, switches, a keyboard, knobs, levers, a display screen, a touch screen, speakers, a microphone, an indicator light, an audible alarm, a printer, and/or other interface devices. In one embodiment, user interface 16 includes a plurality of separate interfaces. In one embodiment, user interface 16 includes at least one interface that is provided integrally with pressure generator 14.

It is to be understood that other communication techniques, either hard-wired or wireless, are also contemplated by the present disclosure as user interface 16. For example, the present disclosure contemplates that user interface 16 is a wireless alarm clock kept by the bedside of subject 12. In this example, information indicating an alarm window of time is entered in the alarm clock by subject 12, wirelessly transmitted to processor 20, and then wirelessly transmitted to pressure generator 14, enabling system 10 to wake subject 12 at an appropriate time. Other exemplary input devices and techniques adapted for use with system 10 as user interface 16 include, but are not limited to, an RS-232 port, RF link, an IR link, modem (telephone, cable or other). In short, any technique for communicating information with system 10 is contemplated by the present disclosure as user interface 16.

In one embodiment, user interface 16 is configured to display previous information entered by subject 12 (or another user), information generated by processor 20, and/or other information to subject 12 or another user. User interface 16 may be configured to suggest recommended alarm windows based on the previously entered and/or generated information. For example, user interface 16 may display information related to prior alarm window set points, alarm window set points relative to actual wake up times, suggested alarm windows, and/or other information. Subject 12 may use the displayed information to set alarm windows for future sleep.

One or more sensors 18 are configured to generate one or more output signals conveying information related to one or more parameters of the pressurized flow of breathable gas. The one or more parameters may include, for example, one or more of a flow rate, a volume, a pressure, a composition (e.g., concentration(s) of one or more constituents), humidity, temperature, acceleration, velocity, acoustics, changes in a parameter indicative of wakefulness, and/or other gas parameters. The sensors 18 may include one or more sensors that measure such parameters directly (e.g., through fluid communication with the pressurized flow of breathable gas at pressure generator 14 or in subject interface 15). The sensors 18 may include one or more sensors that generate output signals related to one or more parameters of the pressurized flow of breathable gas indirectly. For example, one or more of sensors 18 may generate an output based on an operating parameter of pressure generator 14 (e.g., a motor current, voltage, rotational velocity, and/or other operating parameters), and/or other sensors. Although sensors 18 are illustrated at a single location in subject interface 15, this is not intended to be limiting. Sensors 18 may include sensors disposed in a plurality of locations, such as for example, within pressure generator 14, within (or in communication with) conduit 24, within (or in communication with) interface appliance 26, and/or other locations.

Processor 20 is configured to provide information processing capabilities in system 10. As such, processor 20 may include one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 may include a plurality of processing units. These processing units may be physically located within the same device (e.g., pressure generator 14), or processor 20 may represent processing functionality of a plurality of devices operating in coordination (e.g., a processor located within pressure generator 14 and a second processor located within user interface 16).

As shown in FIG. 1, processor 20 is configured to execute one or more computer program modules. The one or more computer program modules may include one or more of a control module 28, a breathing parameter module 30, a wakefulness module 32, an alarm module 34, and/or other modules. Processor 20 may be configured to execute modules 28, 30, 32, and/or 34 by software; hardware; firmware; some combination of software, hardware, and/or firmware; and/or other mechanisms for configuring processing capabilities on processor 20.

It should be appreciated that although modules 28, 30, 32, and 34 are illustrated in FIG. 1 as being co-located within a single processing unit, in implementations in which processor 20 includes multiple processing units, one or more of modules 28, 30, 32, and/or 34 may be located remotely from the other modules. The description of the functionality provided by the different modules 28, 30, 32, and/or 34 described below is for illustrative purposes, and is not intended to be limiting, as any of modules 28, 30, 32, and/or 34 may provide more or less functionality than is described. For example, one or more of modules 28, 30, 32, and/or 34 may be eliminated, and some or all of its functionality may be provided by other ones of modules 28, 30, 32, and/or 34. As another example, processor 20 may be configured to execute one or more additional modules that may perform some or all of the functionality attributed below to one of modules 28, 30, 32, and/or 34.

Control module 28 is configured to control pressure generator 14 to adjust one or more parameters of the pressurized flow of breathable gas based on a therapy regime (e.g., for positive airway pressure support), and/or for other therapeutic purposes. For example, control module 28 may control pressure generator 14 to adjust a flow rate, pressure, volume, humidity, temperature, composition, and/or other parameters of the pressurized flow of breathable gas to maintain an open airway during sleep for subject 12.

Breathing parameter module 30 is configured to determine one or more breathing parameters of subject 12. The one or more breathing parameters are determined based on the one or more output signals generated by sensors 18. The one or more breathing parameters may include, for example, a tidal volume, a peak flow, a flow rate, a pressure, a composition, a timing (e.g., beginning and/or end of inhalation, beginning and/or end of exhalation, etc.), a duration (e.g., of inhalation, of exhalation, of a single breathing cycle, etc.), a breath rate, a respiration frequency, and/or other parameters. In one embodiment, breathing parameter module 30 determines the one or more breathing parameters based on previous respiration by subject 12. By way of a non-limiting example, breathing parameter module 30 may determine at least one breathing parameter for each exhalation in a series of consecutive exhalations. The at least one determined breathing parameter may include, for instance, a tidal volume, a peak flow, and/or other breathing parameters.

By way of another non-limiting example, breathing parameter module 30 may determine at least one average breathing parameter for a series of consecutive exhalations in addition to the breathing parameter determined for each individual exhalation.

Wakefulness module 32 is configured to determine wakefulness of subject 12. During normal sleep a subject may cycle between periods of deeper sleep and periods of lighter sleep. Wakefulness, as determined by wakefulness module 32, is the extent to which a subject is experiencing a period of lighter sleep. Periods of lighter sleep may be indicated by changes in, for example, respiration rate, tidal volume, heart rate, and/or other physical characteristics. The wakefulness of subject 12 may be determined based on output signals from sensors 18 (e.g., physical characteristics related to the breathing of subject 12), one or more breathing parameters determined by breathing parameter module 30, calculation (e.g., a calculated index wherein the algorithm used to calculate the index comprises input related to multiple breathing parameters), and/or other factors.

Output from wakefulness module 32 indicating the wakefulness of subject 12 may comprise a number, a letter, a level (e.g., low, medium, high), and/or other indications. In some embodiments, output from wakefulness module 32 may comprise input to control module 28. In some embodiments, output from wakefulness module 32 may be displayed via user interface 16. Display of the wakefulness of subject 12 via user interface 16 may allow a caregiver, a doctor, and/or another user to utilize the wakefulness information to care for subject 12 and/or for other purposes.

In some embodiments, the wakefulness of subject 12 may be determined based on the one or more output signals from sensors 18. For example, wakefulness may be directly determined from the tidal volume during each individual inhalation and/or exhalation of subject 12 because lower tidal volume indicates lighter sleep. In some embodiments, the wakefulness of subject 12 may be determined based on average breathing parameters calculated from a series of recent inhalations/exhalations and/or output by breathing parameter module 30. In some embodiments, the wakefulness of subject 12 may be determined based on the change over time of output signals from sensors 18 and/or the breathing parameters in module 30. For example, the wakefulness of subject 12 may be determined based on abrupt changes in tidal volume, breath rate, flow shape, or any other signal from sensors 18 and/or information from breathing parameter module 30.

Alarm module 34 is configured to determine an alarm window of time. The alarm window of time may be determined based on user input via user interface 16. The alarm window of time is the period of time during which a user wants subject 12 woken from sleep. For example, a user (e.g., subject 12) may indicate that subject 12 is to be woken from sleep by inputting an alarm window of time start time and an alarm window of time end time via user interface 16. The alarm end time is the time subject 12 is to be woken from sleep even if subject 12 did not experience wakeful sleep (as determined by wakefulness module 32) during the alarm window of time.

In some embodiments a user may input a single wake time and the alarm window of time may be determined from this single entry. For example, alarm module 34 may be configured to begin an alarm window thirty minutes before an entered time and end the alarm window at the entered time. As another example, alarm module 34 may be configured to begin the alarm window of time fifteen minutes before the user entered time, and end the alarm window of time 15 minutes after the user entered time.

In some embodiments the alarm window of time may be determined from a user-entered wake time and a user-entered alarm window of time length. For example, a user may enter a 6 AM wake time and a thirty minute alarm window of time length. In this example, alarm module 34 may be configured to start the alarm window before the wake up time by the user-entered alarm window of time length at 5:30 AM.

In some embodiments, control module 28 is configured to determine a wakefulness threshold and/or to control pressure generator 14 to generate a waking stimulus. The waking stimulus generated by pressure generator 14 is configured to wake subject 12 from sleep (arousal event). Control module 28 is configured to control pressure generator 14 to generate the waking stimulus based on the wakefulness of subject 12 as determined by wakefulness module 32, the alarm window of time, the wakefulness threshold, and/or other factors.

In some embodiments, control module 28 is configured to compare the information indicating wakefulness (output from wakefulness module 32) to a wakefulness threshold and/or an alarm window of time. When the wakefulness of subject 12 breaches the wakefulness threshold within the alarm window of time, control module 28 is configured to control pressure generator 14 to generate a waking stimulus. In some embodiments, breaching may comprise the wakefulness of subject 12 increasing from a level during relatively deep sleep through the wakefulness threshold to another level during relatively light (wakeful) sleep (e.g., the wakefulness threshold indicates lighter stages of sleep). In some embodiments, breaching may comprise the wakefulness of subject 12 decreasing from a level during relatively light sleep through the wakefulness threshold to another level during relatively deep sleep (e.g., the wakefulness threshold indicates deeper stages of sleep). If the wakefulness of subject 12 does not breach the wakefulness threshold during the alarm window of time, control module 28 may be configured to wake subject 12 at a set time (e.g., the end of the alarm window of time). The wake up time may be set by subject 12 via user interface 16.

The waking stimulus may comprise, for example, one or more of modulation of the pressurized flow of breathable gas, sounds (e.g., an alarm noise and/or the radio as with a typical alarm clock), light (e.g., a flashing light and/or increasing light in the room), and/or other stimuli. The waking stimulus may be configured to wake only the subject if the subject is sleeping in proximity to other people. For example, modulating the pressurized flow of breathable gas may be perceived by the subject but not by any others sleeping nearby. The waking stimulus may be generated by pressure generator 14, user interface 16, and/or another device controlled by control module 28 configured to generate a waking stimulus.

Figure 2:
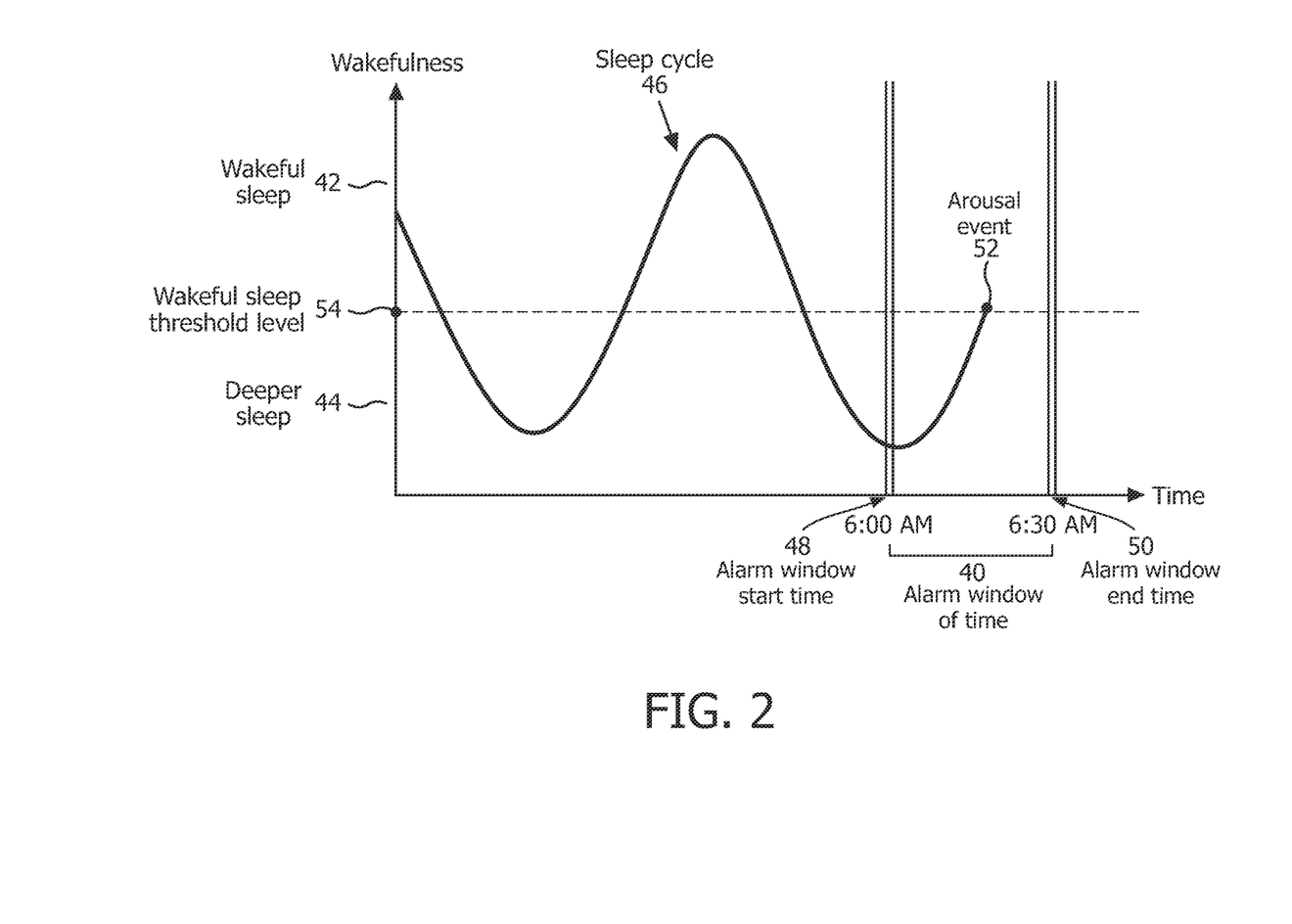
FIG. 2 is a graphical illustration the wakefulness of a subject breaching a wakefulness threshold during an alarm window of time.

By way of a non limiting example, FIG. 2 illustrates an alarm window of time 40, and a wakeful sleep 42/deeper sleep 44 sleep cycle 46. Before going to sleep, a user may set alarm window of time 40 to a time range during which they want to wake up. For example, in FIG. 2, the alarm window of time start time 48 is set to 6:00 AM and the alarm window of time end time 50 is set to 6:30 AM. The present disclosure contemplates using sleep characteristics of the subject gathered during sleep, in combination with user input alarm window of time 40, to wake (arousal event 52) the subject from a period of wakeful lighter sleep 42 (wakeful sleep threshold level 54 breached) during alarm window of time 40.

Wakeful sleep threshold 54 may be determined at manufacture, determined by programming threshold 54 into a processor, determined responsive to information entered by a user via a user interface, determined directly based the one or more output signals generated by one or more sensors, determined based on previous respiration by the subject, and/or determined by another method. For example, wakeful sleep threshold 54 may comprise an average tidal volume calculated from the tidal volume of each breath of the subject during the current sleep period. As another example, wakeful sleep threshold 54 may comprise a maximum tidal volume entered by a user via the user interface.

In one embodiment, wakefulness threshold 54 may vary over time. For example, wakefulness threshold 54 may decrease during alarm window of time 40 as alarm window of time end time 50 is approached. The decreasing threshold may increase the likelihood that the subject wakes from relatively lighter sleep before alarm window of time end time 50 is reached and a waking stimulus is generated whether or not the subject is sleeping lightly or heavily.

Returning to FIG. 1, in some embodiments, electronic storage 22 comprises electronic storage media that electronically stores information. The electronic storage media of electronic storage 22 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 22 may store software algorithms, information determined by processor 20, information received via user interface 16, and/or other information that enables system 10 to function properly. Electronic storage 22 may be (in whole or in part) a separate component within system 10, or electronic storage 22 may be provided (in whole or in part) integrally with one or more other components of system 10 (e.g., user interface 16, processor 20, etc.).

Figure 3:
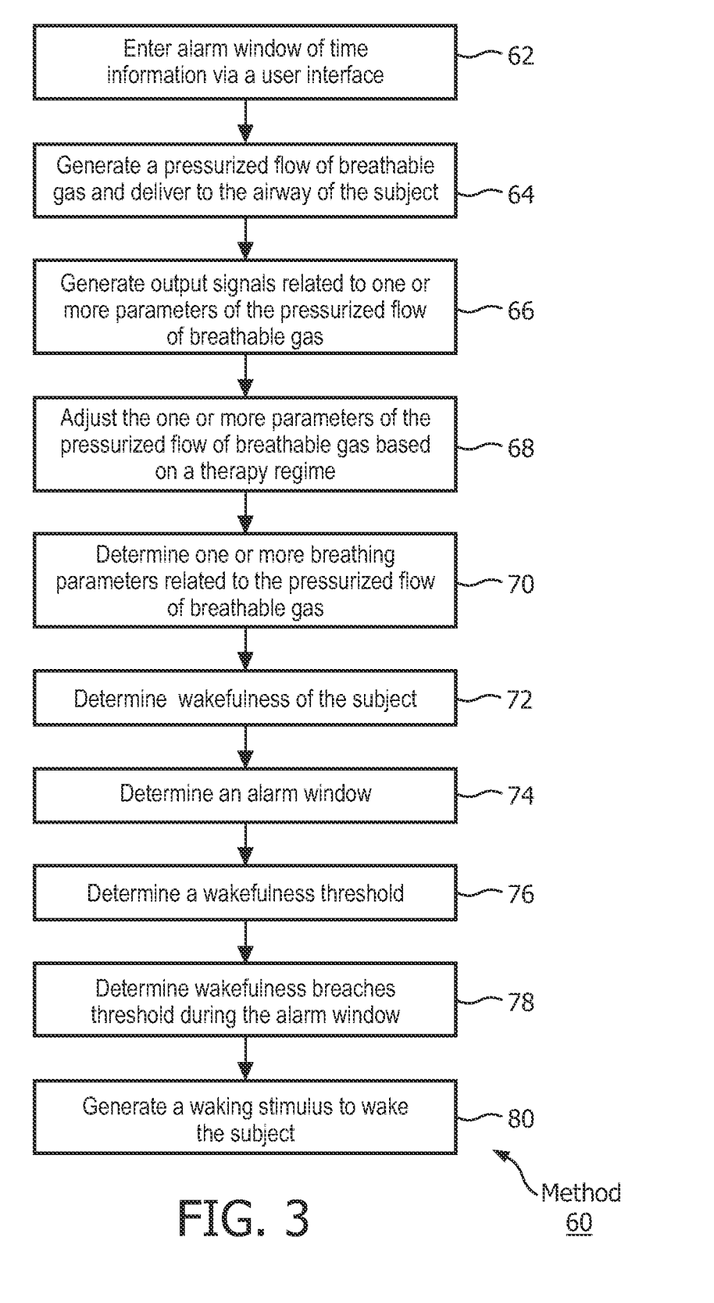
FIG. 3 is a method of waking a subject from wakeful sleep during an alarm window of time.

FIG. 3 illustrates a method 60 of waking a subject from wakeful sleep during an alarm window of time. The operations of method 60 presented below are intended to be illustrative. In some embodiments, method 60 may be accomplished with one or more additional operations not described, and/or without one or more of the operations discussed. Additionally, the order in which the operations of method 60 are illustrated in FIG. 3 and described below is not intended to be limiting.

In some embodiments, method 60 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 60 in response to instructions stored electronically on an electronic storage medium. The one or more processing devices may include one or more devices configured through hardware, firmware, and/or software to be specifically designed for execution of one or more of the operations of method 60.

At an operation 62, a subject enters alarm window of time information via a user interface. The alarm window of time information represents the time period during which the subject is to be woken from sleep. The alarm window of time information may comprise an alarm window of time start time and/or an alarm window of time end time. In some embodiments, operation 62 is performed by a user interface and/or alarm window of time the same as or similar to user interface 16 and/or alarm window of time 40 (shown in FIG. 1 and FIG. 2, and described herein).

At an operation 64, a pressurized flow of breathable gas is generated and delivered to the airway of a subject. In some embodiments, operation 64 is performed by a pressure generator the same as or similar to pressure generator 14, and/or subject interface 15 (shown in FIG. 1 and described herein).

At an operation 66, output signals related to one or more parameters of the pressurized flow of breathable gas are generated. In some embodiments, operation 66 is performed by sensors the same as or similar to sensors 18 (shown in FIG. 1 and described herein.)

At an operation 68, one or more parameters of the pressurized flow of breathable gas are adjusted based on a therapy regime (e.g., for positive airway pressure support). In some embodiments, operation 68 is performed by a control module the same as or similar to control module 28 of processor 20, (shown in FIG. 1 and described herein).

At an operation 70, one or more breathing parameters related to the pressurized flow of breathable gas are determined. In some embodiments, operation 70 is performed by a breathing parameter module the same as or similar to breathing parameter module 30 of processor 20, (shown in FIG. 1 and described herein).

At an operation 72, the wakefulness of the subject is determined Wakefulness is the extent to which a subject is experiencing a period of lighter sleep. In some embodiments, operation 72 is performed by a wakefulness module the same as or similar to wakefulness module 32 of processor 20 (shown in FIG. 1 and described herein).

At an operation 74, an alarm window of time is determined. In some embodiments, operation 74 is performed by an alarm module the same as or similar to alarm module 34 of processor 20 (shown in FIG. 1 and described herein).

At an operation 76, a wakefulness threshold is determined. In some embodiments, operation 76 is performed by a control module the same as or similar to control module 28 of processor 20 (shown in FIG. 1 and described herein).

At an operation 78, the wakefulness of the subject is determined to have breached the wakefulness threshold during the alarm window of time. In some embodiments, operation 78 is performed by a control module the same as or similar to control module 28 of processor 20 (shown in FIG. 1 and described herein).

At an operation 80, a waking stimulus is generated to wake the subject. The waking stimulus may comprise, for example, one or more of modulation of the pressurized flow of breathable gas, sound, light, and/or other stimuli. In some embodiments, operation 80 is performed by a control module, a pressure generator, and/or a user interface the same as or similar to control module 28, pressure generator 14 and/or user interface 16 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

The invention claimed is:

1. A wakeful sleep detection alarm device comprising:
   a pressure generator configured to generate a pressurized flow of breathable gas for delivery to the airway of a subject;
   one or more sensors configured to generate one or more output signals conveying information related to one or more parameters of the pressurized flow of breathable gas; and
   one or more processors configured to execute computer program modules, the computer program modules comprising:
      a wakefulness module configured to determine wakefulness of the subject based on the one or more output signals;
      an alarm module configured to determine an alarm window of time, the alarm window of time being a period of time during which the subject is woken; and
      a control module configured to:
         responsive to the determined wakefulness of the subject breaching a threshold during the alarm window of time, control the pressure generator to generate a waking stimulus, wherein the stimulus comprises modulation of the pressurized flow of breathable gas; and
         responsive to the determined wakefulness of the subject not breaching the threshold during the alarm window of time, decrease the threshold during the alarm window of time as an end of the alarm window of time is approached.

2. The device of claim 1, wherein the computer program modules further comprise a breathing parameter module configured to determine, based on the one or more output signals of the one or more sensors, one or more breathing parameters of the subject, wherein the determination of wakefulness is made based on the breathing parameters determined from the output signals, and wherein the breathing parameters of the subject are determined dynamically based on previous respiration by the subject.

3. The device of claim 1, wherein the alarm window of time is configurable by a user.

4. The device of claim 1, wherein the waking stimulus further comprises one or both of an audible stimulus and/or a visual stimulus.

5. The device of claim 1 further comprising a subject interface configured to deliver the pressurized flow of breathable gas from the pressure generator to an airway of the subject.

6. The device of claim 1, wherein the control module is further configured to, responsive to the determined wakefulness of the subject not breaching the threshold during the alarm window of time, wake the subject at the end of the alarm window of time.

7. A method of waking a subject from sleep during a period of wakeful sleep, the method comprising:
generating a pressurized flow of breathable gas for delivery to an airway of a subject;
generating one or more output signals conveying information related to one or more parameters of the pressurized flow of breathable gas;
determining wakefulness of the subject based on the one or more output signals;
determining an alarm window of time, the alarm window of time being a period of time during which the subject is woken;
responsive to the wakefulness of the subject breaching a threshold level during the alarm window of time, generating a waking stimulus, wherein the stimulus comprises modulation of the pressurized flow of breathable gas; and
responsive to the determined wakefulness of the subject not breaching the threshold during the alarm window of time, decreasing the threshold during the alarm window of time as an end of the alarm window of time is approached.

8. The method of claim 7, further comprising determining, based on the one or more output signals, one or more breathing parameters of the subject during respiration, wherein the determination of wakefulness is made based on the breathing parameters determined from the output signals; and wherein the breathing parameters of the subject are determined dynamically based on previous respiration by the subject.

9. The method of claim 7 further comprising configuration of the alarm window by a user.

10. The method of claim 7 wherein generating the waking stimulus further comprises generating one or both of an audible stimulus and/or a visual stimulus.

11. The method of claim 7 further comprising delivering the pressurized flow of breathable gas from the pressure generator to an airway of the subject.

12. The method of claim 7 further comprising responsive to the determined wakefulness of the subject not breaching the threshold during the alarm window of time, waking the subject at the end of the alarm window of time.

13. A system configured to wake a subject from sleep during a period of wakeful sleep, the system comprising:
means for generating a pressurized flow of breathable gas for delivery to an airway of a subject;
means for generating one or more output signals conveying information related to one or more parameters of the pressurized flow of breathable gas;
means for determining wakefulness of the subject based on the one or more output signals;
means for determining an alarm window of time, the alarm window of time being a period of time during which the subject is woken; and
means for controlling the means for generating a pressurized flow of breathable gas, wherein the means for controlling, is configured to:
responsive to the determined wakefulness of the subject breaching a threshold level during the alarm window of time, generate a waking stimulus, wherein the stimulus comprises modulation of the pressurized flow of breathable gas; and
responsive to the determined wakefulness of the subject not breaching the threshold during the alarm window of time, decrease the threshold during the alarm window of time as an end of the alarm window is approached.

14. The system of claim 13, further comprising means for determining, based on the one or more output signals from the means for generating output signals, one or more breathing parameters of the subject during respiration, wherein the determination of wakefulness is made based on the breathing parameters determined from the output signals, and wherein the breathing parameters of the subject are determined dynamically based on previous respiration by the subject.

15. The system of claim 13 further comprising means for configuring the alarm window of time by a user.

16. The system of claim 13 wherein the means for generating the waking stimulus further comprises generating one or both of an audible stimulus and/or a visual stimulus.

17. The system of claim 13 further comprising means configured to deliver the pressurized flow of breathable gas from the pressure generator to an airway of the subject.

18. The system of claim 13, wherein the means for controlling the means for generating is configured to, responsive to the determined wakefulness of the subject not breaching the threshold during the alarm window of time wake the subject at the end of the alarm window of time.

* * * * *